(12) United States Patent
Hill

(10) Patent No.: US 8,870,842 B2
(45) Date of Patent: Oct. 28, 2014

(54) SANITARY PAD

(75) Inventor: Gretchel Linelia Hill, New York, NY (US)

(73) Assignee: Gretchel Linelia Hill, New York, NY (US)

( * ) Notice: Subject to any disclaimer, the term of this patent is extended or adjusted under 35 U.S.C. 154(b) by 377 days.

(21) Appl. No.: 13/199,234

(22) Filed: Aug. 23, 2011

(65) Prior Publication Data

US 2013/0053808 A1  Feb. 28, 2013

(51) Int. Cl.
*A61F 13/15* (2006.01)
*A61F 13/472* (2006.01)
*A61F 13/475* (2006.01)
*A61F 13/56* (2006.01)

(52) U.S. Cl.
CPC ..... *A61F 13/47218* (2013.01); *A61F 13/47227* (2013.01); *A61F 13/475* (2013.01); *A61F 13/5616* (2013.01)
USPC .................................................. 604/385.17

(58) Field of Classification Search
CPC . A61F 13/47; A61F 13/472; A61F 13/47209; A61F 13/47218; A61F 13/47227; A61F 13/475; A61F 13/4756; A61F 13/476; A61F 13/535; A61F 2013/530437
USPC .................................................. 604/385.17
See application file for complete search history.

(56) References Cited

U.S. PATENT DOCUMENTS

| | | | | |
|---|---|---|---|---|
| 3,115,877 A | * | 12/1963 | Harwood | 604/375 |
| 4,631,062 A | * | 12/1986 | Lassen et al. | 604/385.02 |
| 4,804,380 A | * | 2/1989 | Lassen et al. | 604/385.17 |
| 5,275,591 A | * | 1/1994 | Mavinkurve | 604/387 |
| 6,326,525 B1 | * | 12/2001 | Hamajima et al. | 604/378 |
| 7,279,613 B2 | * | 10/2007 | Nozaki et al. | 604/380 |
| 7,601,144 B2 | * | 10/2009 | Drevik | 604/385.101 |
| 2004/0147895 A1 | * | 7/2004 | Mizutani et al. | 604/385.17 |

* cited by examiner

*Primary Examiner* — Lynne Anderson
(74) *Attorney, Agent, or Firm* — Gretchel Linelia Hill

(57) ABSTRACT

The invention is carried out by forming three embodiment shaped, target zone, externally worn feminine protection sanitary pad, targeting trouble zone leakage between the buttocks, towards the anal and front pubic area. The preferred embodiment absorbent article includes a rear flexible, peak and comfortable raised component liquid absorbent and a front semi-square raise absorbent, raise absorbency will blend from standard center raise absorbent of the pad. Rear peak raise absorbent will fit up against the perineum. The front raise semi-square absorbent is design to cover external area of the pubic mons and clitoris. Alternate preferred embodiment is rear peak raise absorbent, with standard flat front covering the pubic mons and the clitoris exterior. Another alternate embodiment is front semi-square raise absorbent, with standard flat rear. Preferred and alternate embodiments front and rear edges are extended semi-square shape to cover beyond the front and rear of the panty crotch and slightly raise absorbent fold under flaps for center crotch.

23 Claims, 3 Drawing Sheets

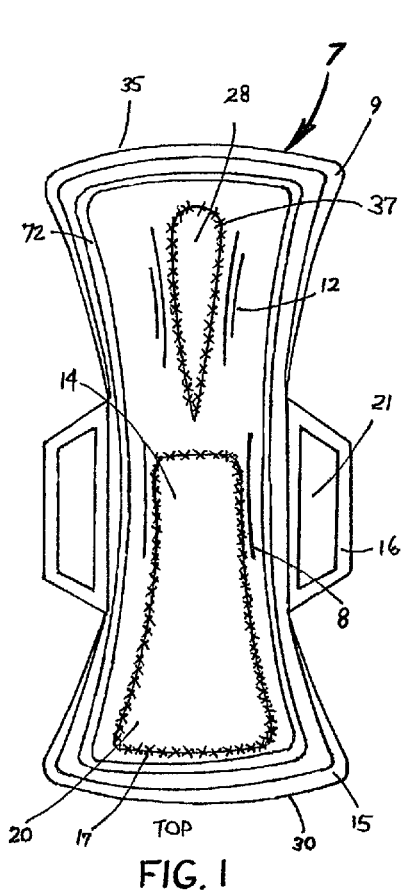
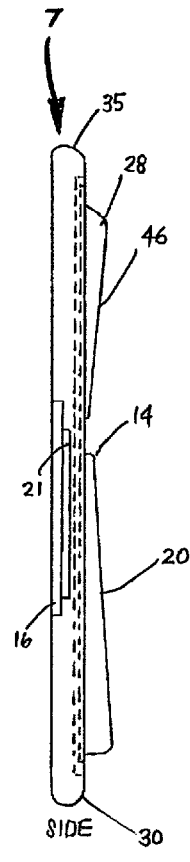
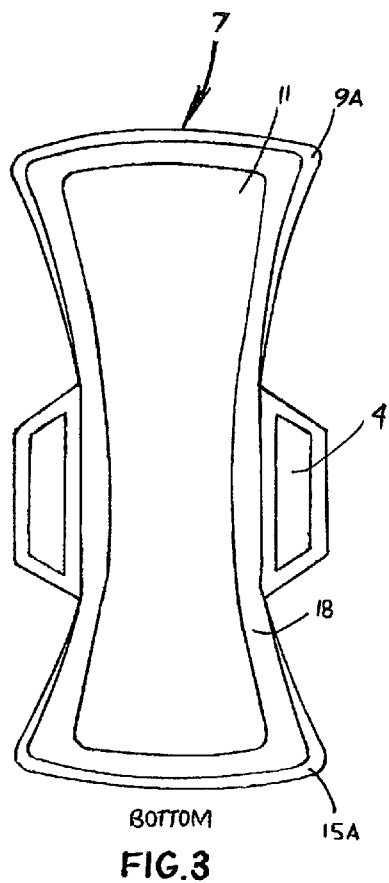
FIG. 1 — TOP
FIG. 2 — SIDE
FIG. 3 — BOTTOM
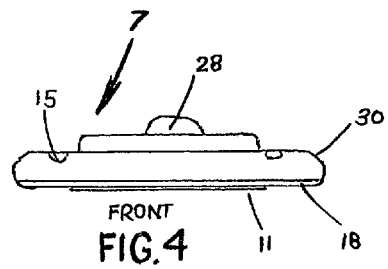
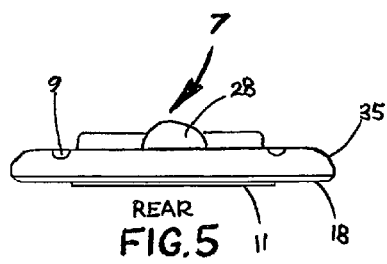
FIG. 4 — FRONT
FIG. 5 — REAR

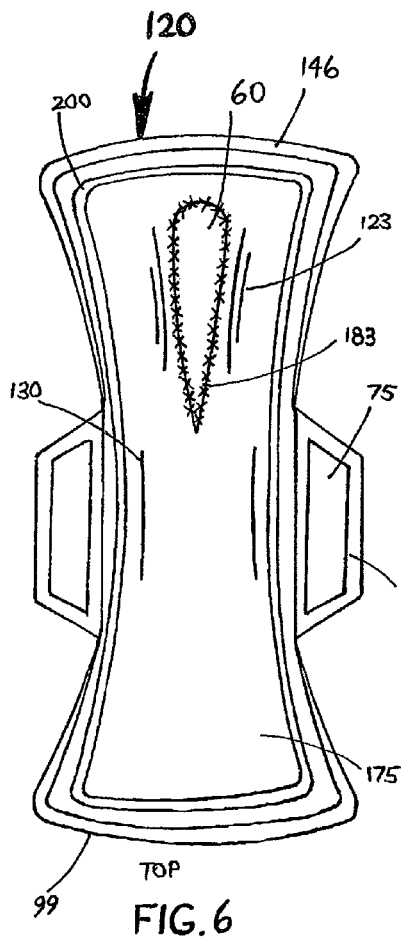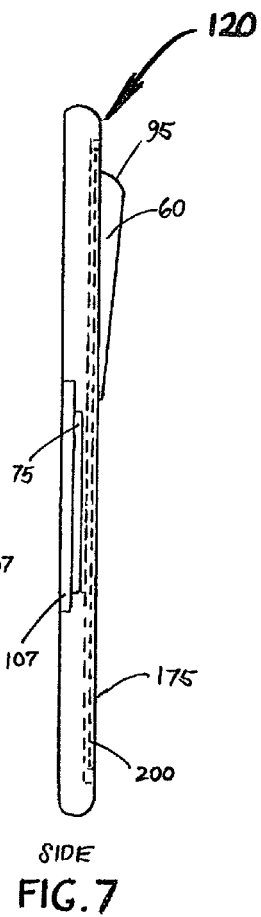
FIG. 6     FIG. 7
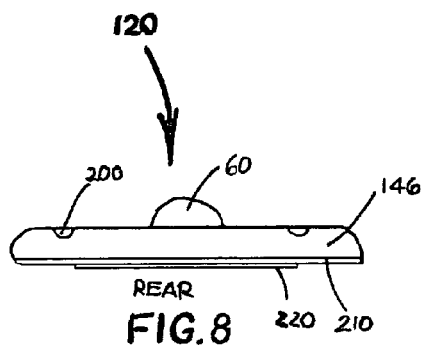
FIG. 8

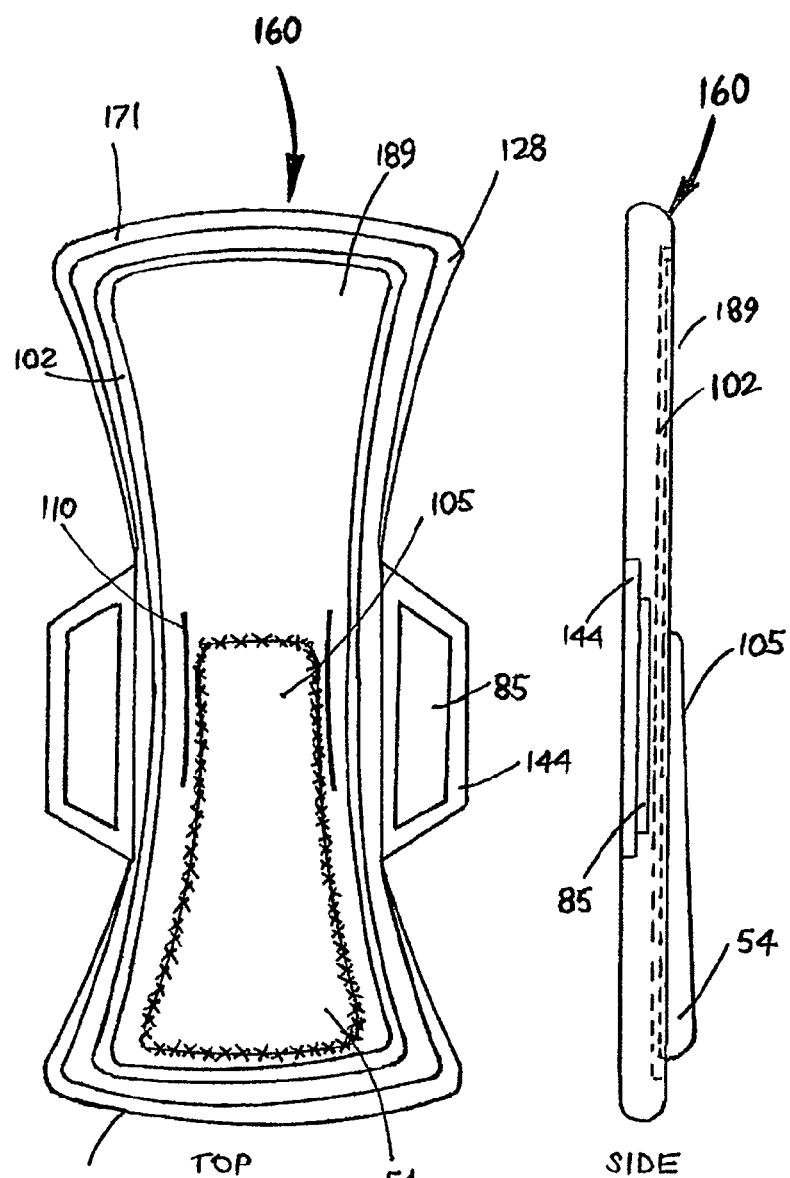
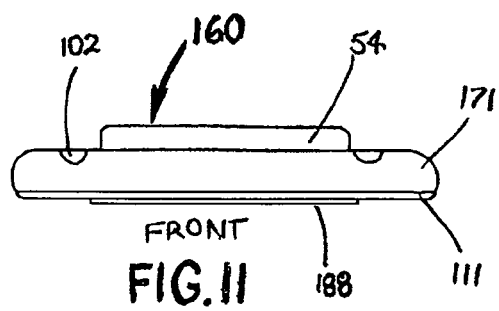

SANITARY PAD

FIELD OF THE INVENTION

The invention relates to personal sanitary products and, in particular, to an absorbent article worn to absorb mild to heavy menstrual fluids and other body secretions. Sanitary pad absorbency will target heavy leakage towards/between the buttocks and anal region and sanitary pad will target mild to heavy flow towards the pubic area region, as well as the vagina area.

BACKGROUND OF THE INVENTION

Absorbing menstrual leakage keeping fluid away from the body and preventing accidents is still the problem that needs improvement with today sanitary pads. There are several sanitary pads that have a tapered hour-glass or rectangular shape, with or without rounded edges. These products are constructed flat with a center raise to absorb menstrual discharge from the vagina area while leaving space available, allowing leakage to flow between the buttock, towards the anus and not enough of absorbent material protection for the clitoris and pubic area. Some women have a heavy leakage flowing between the buttocks towards the anus and some towards the pubic area. After research from speaking to other women, leakage tends to flow more between the buttocks and towards the anus. Uniform flat sanitary pads with center-raised thickness, isn't design to protect, absorb and trap leakage before it reaches the rear side of that area. Menstrual leakage can flow in certain directions, which sometimes flow off the pad on to the underwear and seeping through clothing, especially on the backside of the undergarment. This can be embarrassing, especially in public places. Another drawback is the feeling of wet fluid flowing between the buttocks towards the anus. This is an uncomfortable feeling and can cause irritation and a rash. There's no other extra absorbent protection, sanitary pads designed to absorb menstrual leakage for those hard to reach areas to keep the wearer dry and secure. The point is to feel dry and secure all over.

What has been needed therefore is an absorbent sanitary pad that is designed to absorb leakage in empty unprotected spaces, preventing wetness and soiling, stays dry to the touch, stays secure during sports, activities simply sitting down and sleeping at night, comfortable and to facilitate a woman's anatomy. The improvements and new features are, a unique extra protection 2½"-3" in width and 7"-12" length tapered shape fit for female anatomy sanitary pad with two raised absorbent layers, located front and rear of the preferred embodiment sanitary pad, with 4" wide, extended semi-square, edges located on both ends to protect more of the front and rear undergarment. The preferred embodiment is designed to absorb menstrual leakage while targeting leakage towards the hard to reach areas, between/towards the buttocks anal and clitoris and pubic area. This unique sanitary pad is and far more advance to facilitate a woman's anatomy. It's held in place against the garment surface by removable adhesive and padded flaps. The removable adhesive strip is one strip that is shaped like the pad. The glue/sticky material will hold the sanitary embodiment sturdy and in place without it moving out of place from normal to heavy day to day activity. The preferred embodiment rear absorbent design is a 1½"-2" thick raise/uplift, elongate, narrow tear drop shape and the front absorbent design is a 1"-1½" raise/uplift semi-square. The rear edge sanitary pad is extended 1" beyond the rear 1½"-2" raise/uplift absorbent. The rear elongated uplift raise, narrow tear drop shape absorbent fits against the perineum to act as a dam to absorb fluid flowing towards the rear preventing accidents rashes and wet feeling of fluid. The front 1"-1½" raise/uplift semi-square absorbent is blended in the extended front edge shape of the sanitary pad. Alternate embodiment has a 1½"-2" raise/uplift, elongated, narrow tear drop shape absorbency for heavy leakage between the buttocks and towards the anal area only. Another alternate embodiment has a 1"-1½" raise/uplift semi-square absorbent for heavy leakage towards the clitoris and pubic area blended in with the front semi-square extended edge shape of the pad. The preferred embodiments raised absorbents will blend from center standard raised thickness of the sanitary pad. Sanitary pad and extra absorbency will be surrounded with stitch barriers allowing entire sanitary pad to be utilized. Preferred embodiments can also be used for incontinence protection and any vaginal discharge. Sanitary pad will be designed with absorbent padded flaps to hold pad in place against the panty undergarment for leakage protection for the center of the sanitary pad. Sanitary pad will also be designed to accommodate different sizes and absorbency.

SUMMARY OF THE PRESENT INVENTION

The objection is to invent a target trouble zone, sanitary pad to give extra absorbent protection to absorb menstrual leakage while targeting the hard to reach areas. Another objection is to form more comfort and dry feeling against skin in the hard to reach areas. It solves leakage flowing in one direction, off the pad on to garment surface and clothing, especially on the rear backside not utilizing the entire pad. It solves the feeling of wet fluid flowing between the buttocks towards the anus. It solves the prevention of uncomfortable, itchy irritation and rashes of menstrual leakage towards the rear. A particular advantage of the present invention is that it solves the common psychological assurance against leakage causing accident from simply sitting down to normal everyday activity. This psychologically problem is generally associated with the flat napkins or pads today. Preferred embodiments can also be used for incontinence protection and any vaginal discharge. Therefore to solve and accomplish these problems the invention is designed with a narrow, elongated, raise absorbent material surrounded by stitch barriers located rear on top of sanitary pad. Rear absorbent will fit up against the perineum towards the buttock to absorb and trap mild to heavy menstrual leakage flowing between the buttocks and towards anal region. The rear raise absorbent will conform by the wearer anatomy size and shape and pressure from the wearer against the pad. A semi-square, raise absorbent material surrounded by stitch barriers located front on top of sanitary pad to absorb mild to heavy menstrual leakage towards the clitoris and pubic area. Sanitary pad front and rear edges are extended, semi-square to cover and protect beyond the front and rear thick absorbents and panty crotch. Front and rear raise absorbency on top sanitary pad will blend from center standard raised absorbent. Sanitary pad will be design with absorbent slightly raise absorbent fold under flaps to trap leakage flowing on the sides of center crotch of the sanitary pad. The front raise semi-square absorbent is blended in the extended semi-square edge shape of the sanitary pad. Stitch barriers will allow sanitary pads to be utilized entirely.

BRIEF DESCRIPTION OF THE DRAWING

The Present invention will be understood fully from the detailed description in conjunction with the drawings in which:

FIG. 1 is a top perspective view of sanitary pad;

FIG. 2 is a side view of sanitary pad of FIG. 1;
FIG. 3 is a back view of sanitary pad of FIG. 1;
FIG. 4 is a front view of sanitary pad of FIG. 1;
FIG. 5 is a rear view of sanitary pad of FIG. 1;
FIG. 6 is a top perspective view of alternate sanitary pad;
FIG. 7 is a side view of alternate sanitary pad for FIG. 6;
FIG. 8 is a rear view of alternate sanitary pad of FIG. 6;
FIG. 9 is a top perspective view of alternate sanitary pad;
FIG. 10 is a side view of alternate sanitary pad of FIG. 9;
FIG. 11 is a front view of alternate sanitary pad for FIG. 9;

DETAILED DESCRIPTIONS OF THE
PREFERRED EMBODIMENTS

In the following description, numerous specific details are set forth on order to provide a thorough understanding of the embodiments. It will be obvious, however, to those skilled in the art.

FIG. 1 top perspective view of sanitary pad 7 body surface has 30 semi-square extended front/forward edge and 35 has an extended semi-square edge to cover more of the forward and rear panty crotch. Forward semi-square raise absorbent 20 and 14 narrow center raise will concave to mod and extend generally over the forward portion of the female anatomy in the mons pubic and the forward portion of the labia. The rearward raise peaked absorbent portion 28 extending from 46 rear gradual raise and 46 generally begins in the pudendal cleft rearward portion of the labia adjacent the vestibule and extends to the perineum and slightly ending at the tip before entering between the buttocks and again extended semi-square end beyond the rear peak absorbent to cover more of the panty crotch rear. Center raise absorbent 14 is surrounded by 8 center single side borders. 21 slightly raised absorbents on 16 center flaps of sanitary pad. 72 borders around the inside of the sanitary pad. 9 rear and 15 front edge borders. Rear 28 raise absorbent have 12 double borders on each side to give wearer flexibility. Rear raise absorbent have 37 stitches around raise absorbent to trap and distribute fluid. Front 17 raise absorbent 14 center absorbent has surrounded stitches to trap and distribute fluid. Reference to FIG. 2 is a side view of sanitary pad 7, FIG. 1 has a 35 rear crotch end. Sanitary pad has a 28 raise rear extra absorbency to absorb heavy flow towards and between the buttocks and anal region. 46 gradual raise absorbent to fit against the perineum to catch and absorb leakage towards the rear. 14 centered absorbent is raised gradually to blend in to front raised 20 to absorb and fit against the pubic and clitoris area. 30 front side view edge of pad extends forward for more panty crotch protection. 21 side view of raise absorbent on top of 16 flap to absorb leakage in the center for, especially for gaps. 16 flaps will fold underneath garment.

FIG. 3 back view of sanitary pad 7, FIG. 1. 18 back of sanitary pad bonded sheet. 11 back full adhesive strip to stick to garment surface. Sanitary pad back, with a 9A rear edge and side borders. A back Sanitary pad with a 15A front edge side borders guiding liquid to utilize the entire sanitary pad. 4 back adhesive strip for center flaps to stick to the undergarment beneath center crotch.

FIG. 4 is a front view of sanitary pad 7, is reference to FIG. 1. 20 front raise absorbent view to fit against the pubic and clitoris area. 30 front view of extended edges for the panty crotch area. 28 front view of rear raise absorbent to fit up towards the perineum buttock region. 11 front view of full adhesive strip of FIGS. 3. and 18 front view of bonded sheet from FIG. 3.

FIG. 5 is rear view of sanitary pad 7, FIG. 1. 28 rear raise absorbency to fit up towards the perineum buttock region. 20 rear view of front raise absorbent for the pubic region and 35 rear view of extended edges for panty crotch. 11 rear view of adhesive strip 4 from FIGS. 3. and 18 rear view of bonded sheet from FIG. 3.

FIG. 6 an alternate perspective top view of sanitary pad 120 for rear raise absorbent, to target mild to heavy fluid to towards the rear of sanitary pad. 60 rear raise extra absorbent to fit against the perineum. 95 rear of sanitary pad has a raise extra absorbency to absorb heavy flow towards and between the buttocks and anal region. 146 rear extended semi-square rear edge of sanitary pad for panty crotch. 175 flat front view of sanitary pad absorbent. 99 front end extended semi-square edges beyond and for the panty crotch. 75 raise absorbent on top of center 107 flaps for more absorbency for leakage through gaps. 130 center borders of sanitary pad to help give wearer sanitary pad flexibility. 123 double borders surrounding rear raise absorbent for more flexibility. 183 stitch around the rear raise absorbent to help distribute and trap fluid. Sanitary pad has 200 borders surrounding the inside of the sanitary pad to help distribute fluid and to control leakage on the sides.

FIG. 7 an alternate side view of FIG. 6 sanitary pad 120. 95 rear raise absorbent. 60 rear gradual raise absorbent. 175 flat front of pad. 107 center flaps with 75 raise absorbent on top of flap.

FIG. 8 an alternate rear view of FIG. 6 sanitary pad 120. 60 rear raise absorbent and 146 rear view of extended semi-square edge. 220 rear view of adhesive strip and 210 rear view of bonded sheet.

FIG. 9 alternate perspective top view of sanitary pad 160 for the rear raise absorbent to target mild to heavy fluid towards the front region of the sanitary pad. 171 rear and 101 front extended semi-square edges to cover beyond the undergarment crotch. 128 rear and front 201 edge side borders. 189 rear flat view of pad standard absorbent. Sanitary pad has 102 borders surrounding the inside of sanitary pad to help distribute and control leakage. 110 center single borders to give wearer flexibility. 105 center gradual raise absorbent to fit against the vagina and clitoris area. 54 front raise absorbent to fit against the pubic area. 85 raise absorbent on top of 144 center flaps for more center absorbency. 125 stitches around front raise absorbent 54 and 105 to trap and distribute fluid.

FIG. 10 alternate side view of FIG. 9 sanitary pad 160. 189 rear flat view of pad. 105 center gradual raise absorbent. 54 front raise absorbent. 85 raise absorbent on top of 144 center flaps.

FIG. 11 alternate front view of FIG. 9 sanitary pad 160. 54 front raise absorbent. 171 front extended semi-square edge. 188 front view of back adhesive strip and 111 back bonded sheet. The disposable absorbent sanitary pad can be made with any absorbent material to absorb human exudates such as polyester, cotton, or rayon fibers. Preferred material will have integrity when wet. The preferred embodiment absorbent will have extra layers in two areas, rear and front of sanitary pad. Extra raise absorbent layer for the rear to fit up against the perineum and slightly entering, but ending at the tip between the lower buttocks and extra raise absorbent layer for the front to fit against the pubic body surface. Center absorbent raise layer will be standard for the vagina. The layer absorbent toward the body side for the rear and front/forward density will be different, serving as a transfer layer to trap and distribute fluid utilizing the entire pad. A dry fluid-pervious top sheet, an absorbent core and fluid impervious back sheet. Therefore the layer underneath the permeable cover would be drier and the cover would feel drier to the wearer. The body side, liner permeable material will pass human fluid to the absorbent. The rear raise peak absorbent will be conformed or formed to the raise peak according to the pressure of the wearer, wearing the sanitary pad and the absorbent size of the sanitary pad. The pad will be made were the stitches or dots surrounding the rear raise peak absorbent gives it flexibility to raise as much to fit up against the perineum according to pressure between the wearer legs and the absorbent size and anatomy size of the wearer. With the extended semi-square wide rear edges, it will add extra protection surrounding the rear raise and front absorbent. Conventional materials and machines are used to easily inexpensively manufacture the present invention.

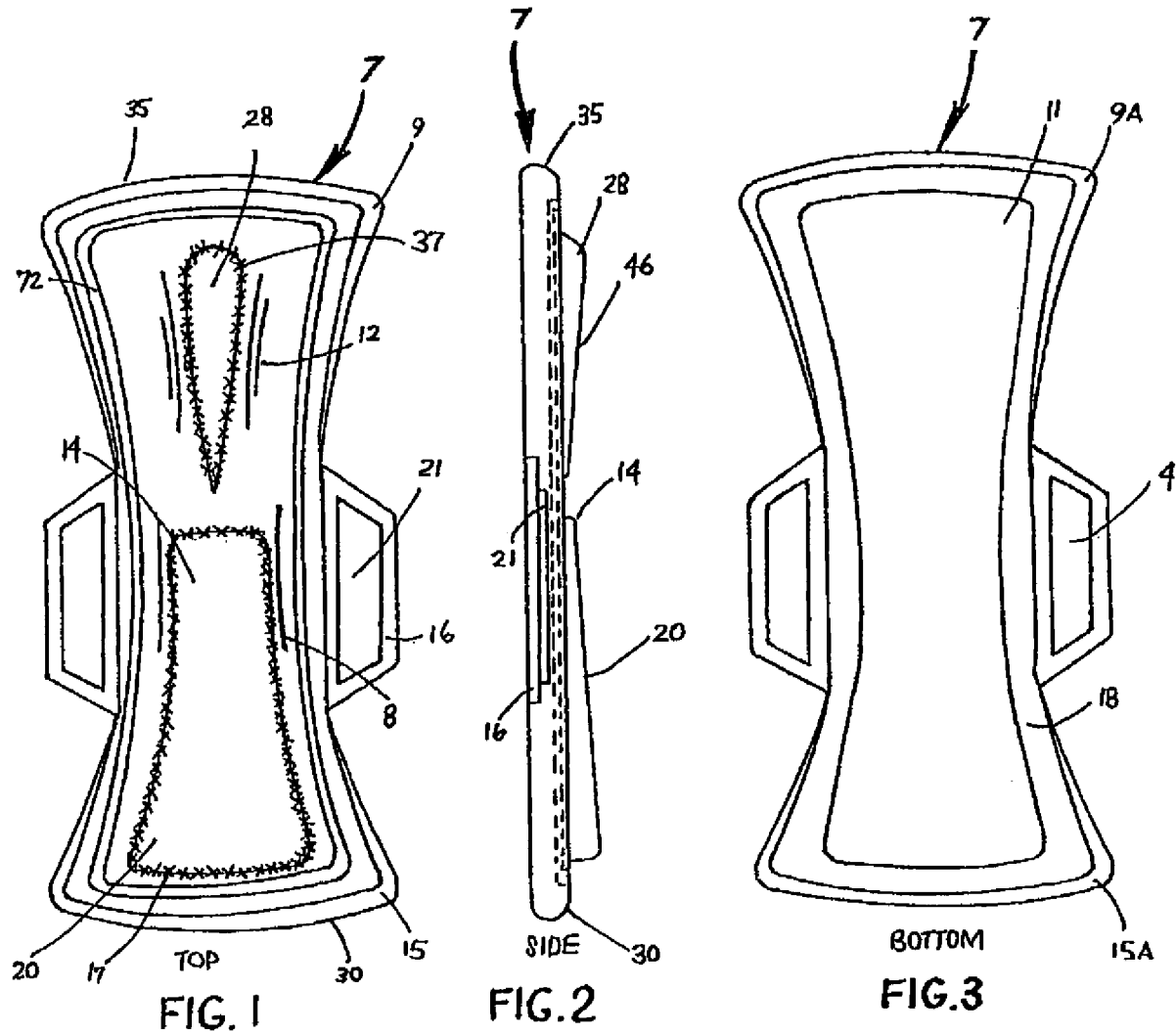
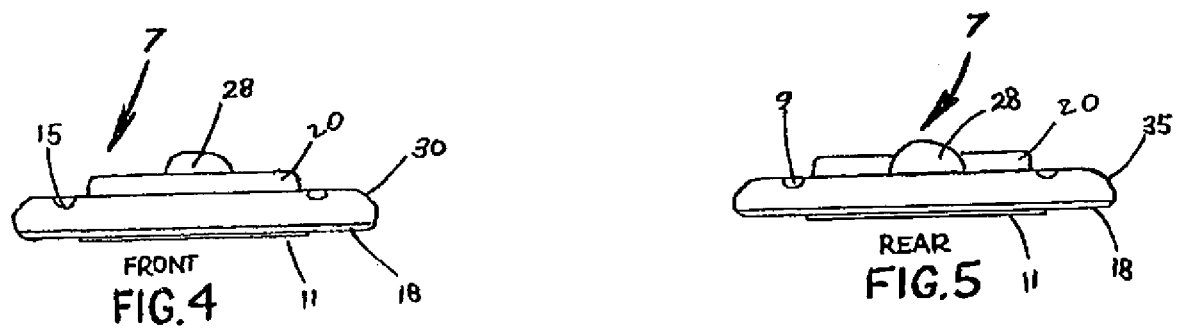

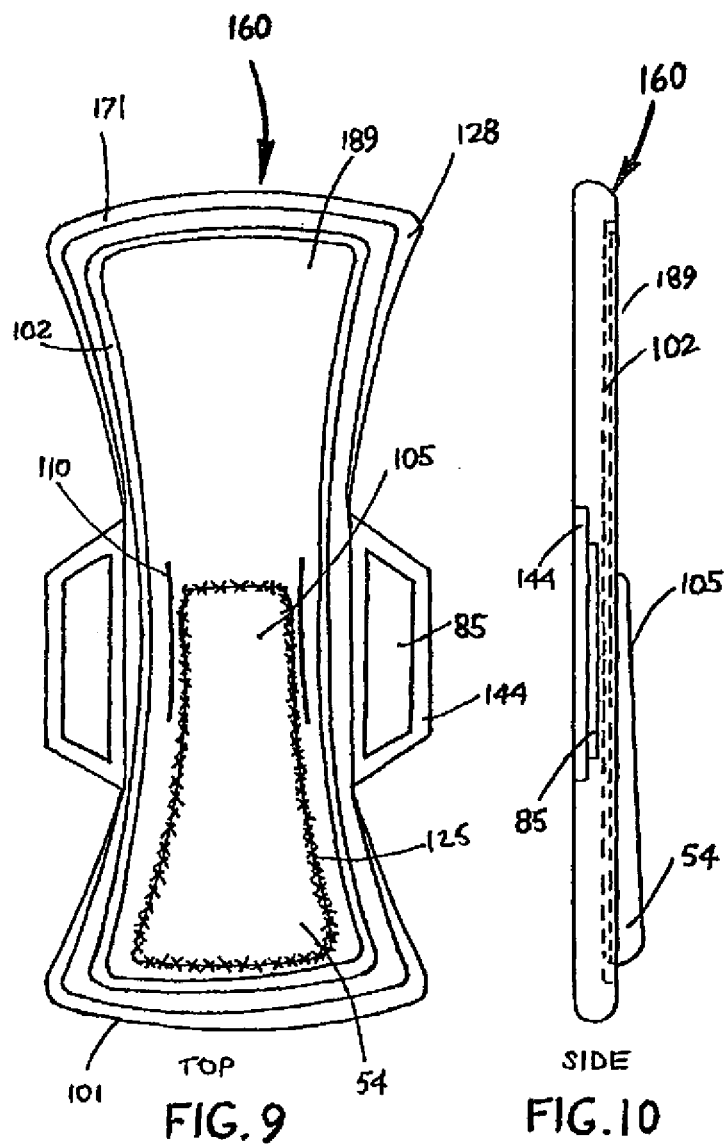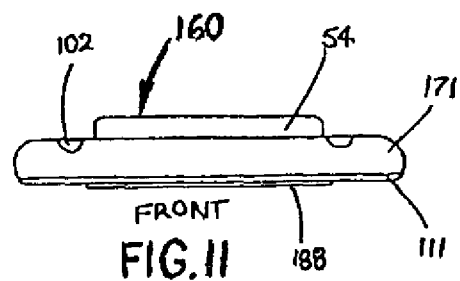

I claim as my invention:

1. A sanitary pad with raised absorbent protection from menstrual leakage, comprising:
    a fluid pervious top sheet;
    a fluid impervious back sheet;
    an absorbent core;
    a rear raised absorbent portion having an elongated teardrop shape located on a top surface of a rear of the sanitary pad, wherein the rear raised absorbent portion tapers gradually from an end closest to a rear end of the sanitary pad towards a center of the sanitary pad;
    a front raised absorbent portion having a semi-square shape, located on the top surface of a front of the sanitary pad, wherein the front raised absorbent portion tapers gradually from the front end of the sanitary pad towards center of the sanitary pad;
    an adhesive strip located on the fluid impervious back sheet of attachment of the sanitary pad to an undergarment;
    padded absorbent flaps located on each side of the center of the sanitary pad to be folded under an undergarment, wherein the padded absorbent flaps comprise flap adhesive strips;
    each of the front and rear raised absorbent portions being surrounded by a stitched leakage border;
    the sanitary pad having semi-square edges located at the front and rear of the sanitary pad;
    the sanitary pad having a single border located on each side of a center of the sanitary pad.

2. The sanitary pad of claim 1, wherein the front raised absorbent portion has a thickness of 0.5-1 inches.

3. The sanitary pad of claim 1, wherein the rear raised absorbent portion has a thickness of 1.5-2 inches.

4. The sanitary pad of claim 1, wherein the sanitary pad has a width of 2.5-3 inches and a length of 7-12 inches.

5. The sanitary pad of claim 1, wherein front and rear lateral ends extend between the semi-square edges, and have a width of 4 inches.

6. The sanitary pad of claim 1, wherein the sanitary pad made in different sizes, material, absorbency for protection capabilities against mild to heavy leakage.

7. The sanitary pad of claim 1, wherein front raised absorbent portion blends in with front lateral semi-square extended edge.

8. The sanitary pad of claim 1, further comprising a leak barrier surrounding the perimeter of the sanitary pad.

9. The sanitary pad of claim 1, further comprising double stitched borders located on either side of the rear raised absorbent portion.

10. A sanitary pad with, alternate raised absorbent protection from menstrual leakage comprising:
    a fluid pervious top sheet;
    a fluid impervious back sheet;
    an absorbent core;
    a rear raised absorbent portion having an elongated teardrop shape located on a top surface of a rear of the sanitary pad, wherein the rear raised absorbent portion tapers gradually from an end closest to a rear end of the sanitary pad towards a center of the sanitary pad, wherein sanitary pad having a flat front absorbent;
    an adhesive strip located on the fluid impervious back sheet of attachment of the sanitary pad to an undergarment;
    padded absorbent flaps located on each side of the center of the sanitary pad to be folded under an undergarment, wherein the padded absorbent flaps comprise flap adhesive strips;
    rear raised absorbent portion being surrounded by a stitched leakage border;
    the sanitary pad having semi-square edges located at the front and rear of the sanitary pad;
    the sanitary pad having a single border located on each side of a center of the sanitary pad.

11. The sanitary pad of claim 10, wherein the rear raised absorbent portion has a thickness of 1.5-2 inches.

12. The sanitary pad of claim 10, wherein the sanitary pad has a width of 2.5-3 inches and a length of 7-12 inches.

13. The sanitary pad of claim 10, wherein front and rear lateral ends extend between the semi-square edges, and have a width of 4 inches.

14. The sanitary pad of claim 10, wherein the sanitary pad made in different sizes, material; and absorbency for protection capabilities against mild to heavy leakage.

15. The sanitary pad of claim 10, further comprising a leak barrier surrounding the perimeter of the sanitary pad.

16. The sanitary pad of claim 10, further comprising double stitched borders located on either side of the rear raised absorbent portion.

17. A sanitary pad of with, alternate raised absorbent protection from menstrual leakage comprising:
    a fluid pervious top sheet;
    a fluid impervious back sheet;
    an absorbent core;
    a front raised absorbent portion having a semi-square shape, located on the top surface of a front of the sanitary pad, wherein the front raised absorbent portion tapers gradually from the front end of the sanitary pad towards center of the sanitary pad, wherein sanitary pad having a flat rear absorbent;
    an adhesive strip located on the fluid impervious back sheet of attachment of the sanitary pad to an undergarment;
    padded absorbent flaps located on each side of the center of the sanitary pad to be folded under an undergarment, wherein the padded absorbent flaps comprise flap adhesive strips;
    a front raised absorbent portions being surrounded by a stitched leakage border;
    the sanitary pad having semi-square edges located at the front and rear of the sanitary pad;
    the sanitary pad having a single border located on each side of a center of the sanitary pad.

18. The sanitary pad of claim 17, wherein the front raised absorbent portion has a thickness of 0.5-1 inches.

19. The sanitary pad of claim 17, wherein the sanitary pad has a width of 2.5-3 inches and a length of 7-12 inches.

20. The sanitary pad of claim 17, wherein front and rear lateral ends extend between the semi-square edges, and have a width of 4 inches.

21. The sanitary pad of claim 17, wherein the sanitary pad made in different sizes, material; and absorbency for protection capabilities against mild to heavy leakage.

22. The sanitary pad of claim 17, further comprising; a leak barrier surrounding the perimeter of the sanitary pad.

23. The sanitary pad of claim 17, wherein front raised semi-square absorbent blends in with front lateral semi-square extended edge.

\* \* \* \* \*

UNITED STATES PATENT AND TRADEMARK OFFICE
CERTIFICATE OF CORRECTION

| | | |
|---|---|---|
| PATENT NO. | : 8,870,842 B2 | Page 1 of 6 |
| APPLICATION NO. | : 13/199234 | |
| DATED | : October 28, 2014 | |
| INVENTOR(S) | : Gretchel Linelia Hill | |

It is certified that error appears in the above-identified patent and that said Letters Patent is hereby corrected as shown below:

In the Drawings

Delete Drawing Sheets 1 and 3 and substitute therefore with the attached Drawing Sheets 1 and 3.
FIGS. 4 and 5 have been amended.

In the Specification

Column 2, lines 22-60 should read as follows:

SUMMARY OF THE PRESENT INVENTION
The object is to invent a target trouble zone, sanitary pad to give extra absorbent protection to absorb menstrual leakage while targeting the hard to reach areas. Another objection is to form more comfort and dry feeling against skin in the hard to reach areas. It solves leakage flowing in one direction, off the pad on to garment surface and clothing, especially on the rear backside not utilizing the entire pad. It solves the feeling of wet fluid flowing between the buttocks towards the anus. It solves the prevention of uncomfortable, itchy irritation and rashes of menstrual leakage towards the rear. A particular advantage of the present invention is that it solves the common psychological assurance against leakage causing accident from simply sitting down to normal everyday activity. This psychologically problem is generally associated with the flat napkins or pads today. Preferred embodiments can also be used for incontinence protection and any vaginal discharge.
Therefore to solve and accomplish these problems the invention is designed with a narrow, elongated, raise absorbent material surrounded by stitch barriers located rear on top of sanitary pad.
Rear absorbent will fit up against the perineum towards the buttock to absorb and trap mild to heavy Signed and Sealed this
Nineteenth Day of May, 2015

Michelle K. Lee
*Director of the United States Patent and Trademark Office* menstrual leakage flowing between the buttocks and towards anal region. The rear raise absorbent will conform by the wearer anatomy size and shape and pressure from the wearer against the pad. A semi-square, raise absorbent material surrounded by stitch barriers located front on top of sanitary pad to absorb mild to heavy menstrual leakage towards the clitoris and pubic area. Sanitary pad front and rear edges are extended, semi-square to cover and protect beyond the front and rear thick absorbents and panty crotch. Front and rear raise absorbency on top sanitary pad will blend from center standard raised absorbent. Sanitary pad will be design with absorbent slightly raise absorbent fold under flaps to trap leakage flowing on the sides of center crotch of the sanitary pad. The front raise semi-square absorbent is blended in the extended semi-square edge shape of the sanitary pad. Stitch barriers will allow sanitary pads to be utilized entirely.

Delete text at Column 3, line 12-Column 5, line 10 and substitute with the following text:

DETAILED DESCRIPTIONS OF THE PREFERRED EMBODIMENTS
In the following description, numerous specific details are set forth on order to provide a thorough understanding of the embodiments. It will be obvious, however, to those skilled in the art. Figure 1 top perspective view of sanitary pad 7 body surface has semi-square extended front/forward edge 30 and rear edge 35 to cover more of the forward and rear panty crotch. Forward semi-square raise absorbent 20 and narrow center raise 14 will concave to mold and extend generally over the forward portion of the female anatomy in the mons pubic and the forward portion of the labia. The rearward raise peaked absorbent portion 28 extending from rear gradual raise 46 and 46 generally begins in the pudendal cleft rearward portion of the labia adjacent the vestibule and extends to the perineum and slightly ending at the tip before entering between the buttocks and again extended semi-square end beyond the rear peak absorbent to cover more of the panty crotch rear. Center raise absorbent 14 is surrounded by center single side borders 8. Slightly raised absorbents 21 on center flaps 16 of sanitary pad. Borders 72 around the inside of the sanitary pad. Rear and front edge borders 9 and 15. Rear raise absorbent 28 have double borders 12 on each side to give wearer flexibility. Rear raise absorbent have stitches 37 around raise absorbent to trap and distribute fluid. Front raise absorbent 20, center absorbent 14 has surrounded stitches 17 to trap and distribute fluid.
FIG. 2 is a side view of sanitary pad 7, is reference to FIG. 1 has a rear crotch end 35. Sanitary pad has a raise rear extra absorbency 28 to absorb heavy flow towards and between the buttocks and anal region. Gradual raise absorbent 46 to fit against the perineum to catch and absorb leakage towards the rear. Centered absorbent 14 is raised gradually to blend in to front raised 20 to absorb and fit against the pubic and clitoris area. Front side view edge 30 of pad extends forward for more panty crotch protection. Side view raise absorbent 21 on top of flap 16 to absorb leakage especially in the center gaps. Flaps 16 will fold underneath garment.

Figure 3 back view of sanitary pad 7 is reference to FIG. 1 back of sanitary pad bonded sheet 18. Back full adhesive strip 11 to stick to garment surface. Sanitary pad back, with a rear edge and side borders 9A. A back Sanitary pad with a 15A front edge side borders guiding liquid to utilize the entire sanitary pad. 4 back adhesive strip for center flaps to stick to the undergarment beneath center crotch.

Figure 4 is a front view of sanitary pad 7, is reference to FIG 1. Front raise absorbent view 20 to fit against the pubic and clitoris area. Front view of extended edges 30 for the panty crotch area. Front view of rear raise absorbent 28 to fit up towards the perineum buttock region. Front view of full adhesive strip 11 of FIG. 3 and front view of bonded sheet 18 from FIG 3.

Figure 5 is rear view of sanitary pad 7, is reference to FIG 1. rear raise absorbency 28 to fit up towards the perineum buttock region. Rear view of front raise absorbent 20 for the pubic region and rear view of extended edges 35 for panty crotch. Rear view of adhesive strip 11 from FIG 3. and rear view of bonded sheet 18 from FIG 3.

Figure 6 an alternate perspective top view of sanitary pad 120 for rear raise absorbent, to target mild to heavy fluid to towards the rear of sanitary pad. Rear raise extra absorbent 60 to fit against the perineum. Rear of sanitary pad has a raise extra absorbency 95 to absorb heavy flow towards and between the buttocks and anal region. Rear extended semi-square rear edge 146 of sanitary pad for panty crotch. Flat front view 175 of sanitary pad absorbent. Front end extended semi-square edges 99 beyond and for the panty crotch. Raise absorbent 75 on top of center flaps 107 for more absorbency for leakage through gaps. Center borders 130 of sanitary pad to help give wearer sanitary pad flexibility. Double borders 123 surrounding rear raise absorbent for more flexibility. Stitches 183 around the rear raise absorbent to help distribute and trap fluid. Sanitary pad has borders 200 surrounding the inside of the sanitary pad to help distribute fluid and to control leakage on the sides.

Figure 7 an alternate side view of fig 6 sanitary pad 120. Rear raise absorbent 95. Rear gradual raise absorbent 60. Flat front 175 of pad. Center flaps 107 with raise absorbent 75 on top of flap.

Figure 8 an alternate rear view of fig 6 sanitary pad 120. Rear raise absorbent 60 and rear view of extended semi-square edge 146. Rear view of adhesive strip 220 and rear view of bonded sheet 210.

Figure 9 alternate perspective top view of sanitary pad 160 for the rear raise absorbent to target mild to heavy fluid towards the front region of the sanitary pad. Rear and front extended semi-square edges 171 and 101 to cover beyond the undergarment crotch. Rear and front edge side borders 128 and 101. Rear flat view 189 of pad standard absorbent. Sanitary pad has borders 102 surrounding the inside of sanitary pad to help distribute and control leakage. Center single borders 110 to give wearer flexibility. Center gradual raise absorbent 105 to fit against the vagina and clitoris area. Front raise absorbent 54 to fit against the pubic area. Raise absorbent 85 on top of center flaps 144 for more center absorbency.

Stitches 125 around front raise absorbent 54 and 105 to trap and distribute fluid.

Figure 10 alternate side view of fig 9 sanitary pad 160. Rear flat 189 view of pad. Center gradual raise absorbent 105. Front raise absorbent 54. Raise absorbent 85 on top of center flaps 144.

Figure 11 alternate front view of fig 9 sanitary pad 160. Front raise absorbent 54. Front extended semi-square edge 171. Front view of back adhesive strip 188 and back bonded sheet 111.

The disposable absorbent sanitary pad can be made with any absorbent material to absorb human exudates such as polyester, cotton, or rayon fibers. Preferred material will have integrity when wet. The preferred embodiment absorbent will have extra layers in two areas, rear and front of sanitary pad. Extra raise absorbent layer for the rear to fit up against the perineum and slightly entering, but ending at the tip between the lower buttocks and extra raise absorbent layer for the front to fit against the pubic body surface. Center absorbent raise layer will be standard for the vagina. The layer absorbent toward the body side for the rear and front/forward density will be different, serving as a transfer layer to trap and distribute fluid utilizing the entire pad. A dry fluid-pervious top sheet, an absorbent core and fluid impervious back sheet. Therefore the layer underneath the permeable cover would be drier and the cover would feel drier to the wearer. The body side, liner permeable material will pass human fluid to the absorbent. The rear raise peak absorbent will be conformed or formed to the raise peak according to the pressure of the wearer, wearing the sanitary pad and the absorbent size of the sanitary pad. The pad will be made were the stitches or dots surrounding the rear raise peak absorbent gives it flexibility to raise as much to fit up against the perineum according to pressure between the wearer legs and the absorbent size and anatomy size of the wearer. With the extended semi-square wide rear edges, it will add extra protection surrounding the rear raise and front absorbent. Conventional materials and machines are used to easily inexpensively manufacture the present invention.